United States Patent [19]

Kameswaran

[11] Patent Number: 5,008,403

[45] Date of Patent: Apr. 16, 1991

[54] DEACYLATIVE BROMINATION PROCESS FOR THE PREPARATION OF MOLLUSCICIDAL 2,4,5-TRIBROMOPYRROLE-3-CARBONITRILE COMPOUNDS

[75] Inventor: Venkataraman Kameswaran, Princeton Junction, N.J.

[73] Assignee: American Cyanamid Company, Stamford, Conn.

[21] Appl. No.: 447,961

[22] Filed: Dec. 7, 1989

[51] Int. Cl.$^5$ .................... C07B 39/00; C07D 207/34
[52] U.S. Cl. .................................................. 548/561
[58] Field of Search ........................................ 548/561

[56] References Cited

PUBLICATIONS

*Merck Index,* 11th Edition, p. 1268.
1990–1991 Aldrich catalogue.
Fieser & Fieser, Reagents for Organic Synthesis, vol. 1, p. 967 (1987).
Katritzky, "Comprehensive Heterocyclic Chemistry", vol. 4, p. 215 (1983).
A. M. van Leusen et al., Tetrahedron Letters, 5337 (1972).
C. E. Loader et al., Canadian Journal of Chemistry, 59, 2673 (1981).
H. J. Anderson et al., Synthetic Communications, 17, 401 (1987).
P. E. Sonnett, Journal of Medicinal Chemistry, 1972, 15, pp. 97–98.

*Primary Examiner*—Mark L. Berch
*Attorney, Agent, or Firm*—Carmella A. O'Gorman

[57] ABSTRACT

There is provided a method of preparation of 2,4,5-tribromopyrrole-3-carbonitrile compounds in a single deacylative bromination step from their 2-trihaloacetyl-pyrrole-4-carbonitrile precursors. The 2,4,5-tribromopyrrole-3-carbonitrile compounds are useful as molluscicidal agents.

9 Claims, No Drawings

DEACYLATIVE BROMINATION PROCESS FOR THE PREPARATION OF MOLLUSCICIDAL 2,4,5-TRIBROMOPYRROLE-3-CARBONITRILE COMPOUNDS

BACKGROUND OF THE INVENTION

Pyrrole carbonitrile and nitropyrrole compounds useful as acaricides, insecticides and mollusoicide s are described in copending patent application Ser. No. 430,601, filed on Nov. 6, 1989 which is a continuation-in-part of patent application Ser. No. 279,909, filed on Dec. 5, 1988. Molluscicidal 2,4,5-tribromopyrrole-3-carbonitrile and its preparation via bromination of pyrrole-3-carbonitrile are described in the above-said patent applications. However, synthesis of pyrrole-3-carbonitrile is difficult to achieve. Literature methods such as that reported by A. M. van Leusen, et al, Tetrahedran Letters 5337(1972) report yields of 10% or less.

An alternative route to obtain pyrrole-3-carbonitrile is described by H. J. Anderson et al, Canadian Journal of Chemistry, 59, 2673(1981) and Synthetic Communications, 17, 401 (1987) and involves the separate steps of hydrolysis of 2-trichloroacetylpyrrole-4-carbonitrile give 4-cyanopyrrole-2-carboxylic acid, and conversion of the carboxylic acid to pyrrole-3-carbonitrile via a decarboxylation procedure involving a copper chromite catalyst in hot quinoline. However, this procedure may be difficult to control and complex in work-up on a commercial scale.

It is an object of the present invention to provide an efficient and easily controlled process for the preparation of molluscicidal 2,4,5-tribromopyrrole-3-carbonitrile compounds via a single step deacylative bromination of the 2-trihaloacetylpyrrole-4-carbonitrile precursors.

SUMMARY OF THE INVENTION

The present invention relates to a process for the preparation of molluscicidal 2,4,5-tribromopyrrole-3-carbonitrile compounds of formula I

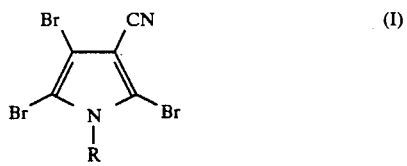

wherein R is hydrogen or $C_1$–$C_6$ alkyl. Said compounds and their molluscicidal use are described in copending patent application Ser. No. 430,601, filed on Nov. 6, 1989, which is a continuation-in-part of patent application Ser. No. 279,909, filed on Dec. 5, 1988 and which is incorporated herein by reference thereto.

Surprisingly it has been found that molluscicidal compounds of formula I are prepared in good yield by an efficient and controlled process via a single step deacylative bromination of compounds of formula II

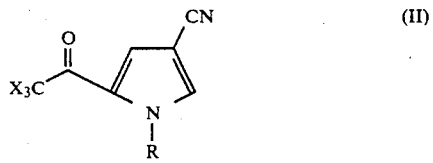

wherein R is as described above and x is fluorine or chlorine. Optionally, the compound of formula II wherein R is hydrogen is deacylatively brominated and then alkylated with the appropriate alkylating agent to give the corresponding alkylated formula I compounds.

DETAILED DESCRIPTION OF THE INVENTION

The present invention provides a process for the preparation of molluscicidal compounds of formula I

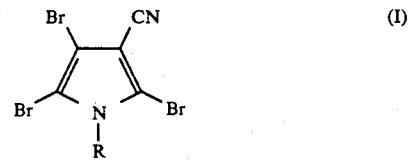

wherein R is hydrogen or $C_1$ to $C_6$ alkyl in a controlled and efficient single step deacylative bromination of compounds of formula II

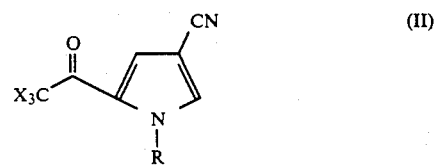

wherein R is as described for formula I and X is fluorine or bromine. The process comprises reacting a formula II pyrrole as described above with about 5 to 10 molar equivalents, preferably about 6 molar equivalents, of a base and about 2 to 4 molar equivalents, Preferably about 3 molar equivalents, of a brominating agent in the presence of a solvent at a temperature range of about 0° to 35° C. to form 2,4,5-tribromopyrrole-3-carbonitrile compounds of formula I. The product formula I compounds are isolated by dilution of the reaction mixture with water, acidification of the diluted reaction mixture and filtration of the formula I product or extraction of said product With a suitable solvent.

Bases suitable for use in the process of the invention are bases such as alkali metal hydroxides, alkali metal carbonates, sodium acetate and pyridine. Preferred bases include bases such as sodium hydroxide, sodium carbonate and sodium acetate. Brominating agents such as bromine, pyridinium bromide perbromide and N-bromosuccinimide may be employed. The preferred brominating agent is bromine. Reaction solvents suitable for use in the above-described process are Water, water and acetic acid, dioxane, tetrahydrofuran and combinations thereof. In the isolation procedure, the acidification of the diluted reaction mixture is achieved using mineral acids such as hydrochloric or sulfuric acids, alkyloarboxylic acids such as acetic acid, and the like. Suitable extraction solvents include water immiscible solvents such as ethyl acetate, methylene chloride, ether, toluene and the like.

Alternatively, compounds of formula I wherein R is not hydrogen may be prepared by reacting compounds of formula II wherein R is hydrogen with about 5 to 10, preferably about 6, molar equivalents of a base and about 2 to 4, preferably about 3 molar equivalents of a brominating agent in the presence of a solvent to form 2,4,5-tribromopyrrole-3-carbonitrile, diluting and acidifying the reaction mixture and isolating the 2,4,5-tribromo-3-carbonitrile by standard techniques such as filtration or extraction with a suitable solvent and reacting said product with an appropriate alkylating agent such as a $C_1-C_6$ alkyl halide in the presence of alkali metal alkoxide to give the desired formula I compound wherein R is not hydrogen.

The starting 2-haloacetylpyrrole-4-carbonitrile compounds are well known in the art and are prepared according to the methods described by P. E. Sonnet, Journal of Medicinal Chemistry, 1972, 15, pp 97-98 and C. E. Loader and H. J. Anderson, Canadian Journal of Chemistry, 59, 2673 (1981).

In order to facilitate a further understanding of the invention, the following examples are presented to illustrate more specific details thereof. The invention is not to be limited thereby except as defined in the claims. NMR designates nuclear magnetic resonance spectroscopy.

EXAMPLE 1

Preparation of 2,4,5-tribromopyrrole-3-carbonitrile from 2-trichloroacetylpyrrole-4-carbonitrile using 3 equivalents of bromine and 6 equivalents of sodium hydroxide

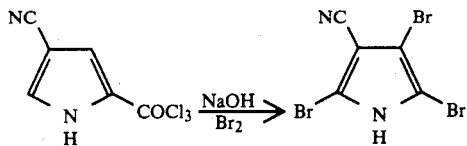

A stirred solution of 2-trichloroacetylpyrrole-3-carbonitrile (7.12 g, 0.03 mol) in dioxane is treated with 50% NaOH (9.6 g, 0.12 mol NaOH) at 10°-17° C. and then treated dropwise with bromine (14.4 g, 0.09% mol) at 10° to 20° C. The pH of the reaction mixture is adjusted to 8.0-8.5 with an additional 0.06 mol of NaOH as a 50% aqueous solution. The reaction mixture is stirred at room temperature for 1 hour and at 50° C. for 1 hour, then cooled to room temperature and diluted with ice Water and ether. The reaction mixture is separated, the aqueous phase is cautiously acidified with concentrated HCl and filtered. The solid filter cake is washed with water and dried in vacuo to give the title product as a broWn solid, 8.0 g (81.1% yield) identified by $^1H$ and $^{13}CNMR$.

Preparation of 2,4,5-tribromopyrrole-3-carbonitrile from 2-trifluoroacetylpyrrole-4-carbonitrile using bromine and sodium hydroxide

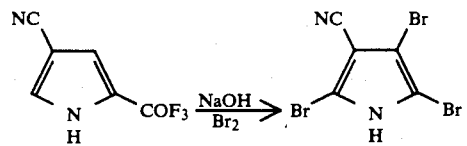

A stirred solution of 2-trifluoroacetylpyrrole-3-carbonitrile (0.94 g, 5.0 mol) in dioxane is treated with 50% NaOH (1.2 g, 15 mmol) at room temperature then treated dropwise with bromine (1.6 g, 10 mmol) (exotherm to 60° C.). The reaction mixture is treated with additional 50% NaOH solution to a slightly alkaline pH, stirred at room temperature for 5 hours, diluted with water, acidified with aqueous HCl and extracted with ether. The combined ether extracts are washed with water, dried over $MgSO_4$ and concentrated in vacuo to give a yellow solid residue. The residue is recrystallized from ethyl acetate/hexane to give the title product as a yellow solid, 0.78 g (47.4%) identified by $^1H$ and $^{13}CNMR$.

Using the above procedure and employing 3 equivalents of bromine and 4 equivalents of NaOH, 2,4,5-tribromopyrrole-3-carbonitrile is obtained as a yellow solid in 37.2% yield after recrystallization.

EXAMPLE 3

Preparation of 2,4,5-tribromopyrrole-3-carbonitrile from 2-trifluoroacetylpyrrole-4-carbonitrile using 2 equivalents of bromine and 2 equivalents of sodium hydroxide

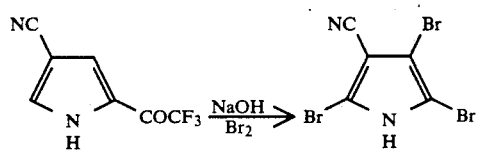

A solution of 2-trifluoroacetylpyrrole-4-carbonitrile (1.88 g, 0.01 mol) in dioxane at 10° C. is treated with 50% aqueous NaOH (1.6 g, 0.02 mol NaOH), stirred for 15 minutes, treated dropwise with bromine (3.2 g, 0.02 mol) at 10°-15° C., stirred for 2 hours at 10° C. and diluted with water and ethyl acetate. The phases are separated and the organic phase is washed with water and saturated NaCl solution, dried over $MgSO_4$ and concentrated in vacuo to give a residue. The residue is slurried in ether to give the title product as a white solid, 1.18 g (35.9%) identified by $^1H$ and $^{13}CNMR$.

EXAMPLE 4

Preparation of 2,4,5-tribromopyrrole-3-carbonitrile from 2-trifluoroacetylpyrrole-4-carbonitrile using pyridinium bromide perbromide

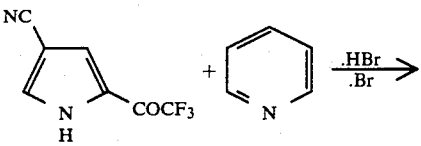

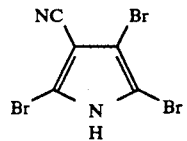

A solution of 2-trifluoroacetylpyrrole-4-carbonitrile (1.88 g, 0.01 mol) in tetrahydrofuran is treated portion wise with pyridinium bromide perbromide (6.4 g, 0.02 mol) at 10° C., stirred at room temperature for 2½ hours, poured into ice water and the resultant mixture is extracted with ethyl acetate. The ethyl acetate extracts are combined, washed sequentially with Water, saturated sodium bicarbonate solution and brine, dried ($MgSO_4$) and concentrated in vacuo to give a pink solid residue. The residue is triturated under ether and filtered to give the title compound as a white solid, 0.04 g (25.5%).

EXAMPLE 5

Preparation of
2,4,5-tribromo-1-methylpyrrole-3-carbonitrile from
2-trichloroacetyl-1-methylpyrrole-4-carbonitrile using
3.2 equivalents of bromine and 8.0 equivalents of NaOH

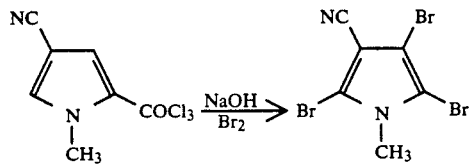

A solution of 2-trichloroacetyl-1-methylpyrrole-4-carbonitrile (3.0 g, 0.012 mol) in dioxane is treated dropwise at 5° to 14° C. with a cold solution of 50% sodium hydroxide (7.83 g, 0.095 mol NaOH) plus water and bromine (6.30 g, 0.038 mol), stirred at room temperature for 1 hour, diluted with water, acidified with dilute HCl and extracted with ethyl acetate. The ethyl acetate extracts are combined, washed sequentially with water, aqueous sodium metabisulfite, water and brine, dried (MgSO$_4$) and concentrated in vacuo to give a white solid residue. The residue is recrystallized from ethyl acetate/hexanes to yield the title product as a crystalline white solid, 2.8 g (68.6%), mp 150°-151° C., identified by $^1$HNMR.

EXAMPLE 6

Preparation of
2,4,5-tribromo-1-methylpyrrol-3-carbonitrile from
2,4,5-tribromopyrrole-3-carbonitrile

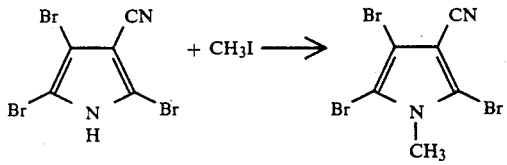

A solution of 2,4,5-tribromopyrrole-3-carbonitrile (103.5 g, 0.315 mol) in anhydrous tetrahydrofuran is treated portionwise with potassium t-butoxide (42.4 g, 0.378 mol) at <40° C., stirred at ambient temperatures for 30 minutes, treated dropwise with methyl iodide (67.0 g, 0.472 mol) over 30 minute period, stirred at room temperature for 2 hours and concentrated in vacuo. The reaction concentrate is diluted with ethyl acetate and water. The phases are separated, the aqueous phase is further extracted with ethyl acetate. The organic phases are combined, washed sequentially with water, 5% NaOH solution, water and brine, concentrated and triturated with hexanes to afford a solid. The solid is recrystallized from ethyl acetate to give a white solid, mp 150.5°-152.0°0 C., identified by $^1$H and $^{13}$CNMR.

I claim:

1. A process for the preparation of a compound having the structure:

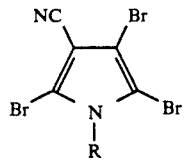

wherein R is hydrogen or C$_1$-C$_6$ alkyl which comprises reacting a compound having the structure:

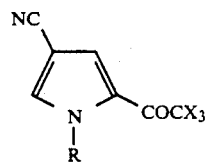

wherein R is hydrogen or C$_1$ to C$_6$ alkyl and X is fluorine or chlorine with at least about 5 molar equivalents of a base and at least about 2 molar equivalents of a brominating agent in the presence of a solvent.

2. The process according to claim 1 wherein the base is selected from the group consisting of alkali metal hydroxides, alkali metal carbonates, pyridine and sodium acetate.

3. The process according to claim 1 wherein the brominating agent is selected from the group consisting of bromine, pyridinium bromide perbromide and N-bromosuccinimide.

4. The process according to claim 1 wherein the reaction solvent is selected from the group consisting of water, water and lower alkyl carboxylic acid, tetrahydrofuran, dioxane and combinations thereof.

5. The process according to claim 1 wherein the base is present in the amount of about 5 to 10 molar equivalents and the brominating agent is present in the amount of about 2 to 4 molar equivalents.

6. The process according to claim 1 wherein the base is an alkali metal hydroxide and is present at about 6 to s molar equivalents and the brominating agent is bromine and is present at about 3.0 to 3.5 molar equivalents.

7. The process according to claim 6 wherein R is hydrogen or methyl.

8. The process according to claim 7 wherein R is methyl.

9. The process according to claim 1 wherein the temperature of the reaction is about 0° to 35° C.

* * * * *

UNITED STATES PATENT OFFICE
CERTIFICATE OF CORRECTION

Patent No. 5,008,403              Dated April 16, 1991

Inventor(s) Venkataraman Kameswaran

It is certified that error appears in the above-identified patent and that said Letters Patent is hereby corrected as shown below:

Claim 6

6. The process according to claim 1, wherein the base is an alkali metal hydroxide and is present at about 6 to 8 molar equivalents and the brominating agent is bromine and is present at about 3.0 to 3.5 molar equivalents.

Signed and Sealed this

Twenty-ninth Day of September, 1992

*Attest:*

DOUGLAS B. COMER

*Attesting Officer*     Acting Commissioner of Patents and Trademarks